United States Patent [19]

Sanning

[11] Patent Number: 5,171,307
[45] Date of Patent: Dec. 15, 1992

[54] IRRIGATION SOLUTION COLLECTION DEVICE

[76] Inventor: Frank B. Sanning, 145 Warren Purcell Rd., Leitchfield, Ky. 42754

[21] Appl. No.: 525,704

[22] Filed: Jun. 11, 1990

[51] Int. Cl.⁵ .................... A61M 1/00; A61M 35/00
[52] U.S. Cl. ................................ 661/327; 604/355;
604/319; 604/289; 604/294; 661/297; 128/760
[58] Field of Search ........ 128/849, 853, 854, 760-762,
128/767, 768, 847, 850, 856; 604/19, 48, 284,
302, 313, 317, 319, 322, 327, 355, 357, 358,
378-383, 49, 73; 433/136-139

[56] References Cited
U.S. PATENT DOCUMENTS

| 830,608 | 9/1906 | Magill . | |
|---|---|---|---|
| 1,121,667 | 12/1914 | Ross . | |
| 1,966,557 | 7/1934 | Michelson . | |
| 2,658,512 | 11/1953 | Tcheong | 604/357 |
| 2,910,064 | 10/1959 | Brangaitis | 609/301 |
| 3,650,267 | 3/1972 | Anderson | 128/853 |
| 3,658,065 | 4/1972 | Hirsch | 604/327 |
| 3,664,340 | 5/1972 | Morgan . | |
| 3,743,536 | 7/1973 | Russell | 604/369 |
| 3,918,433 | 11/1975 | Fuisz | 128/760 |
| 3,935,863 | 2/1976 | Kliger | 604/369 |
| 4,098,728 | 7/1978 | Rosenblatt | 604/369 |
| 4,136,036 | 1/1979 | Columbus | 128/760 |
| 4,246,901 | 1/1981 | Michaud | 604/329 |
| 4,525,166 | 6/1985 | Leclerc | 604/813 |
| 4,553,966 | 11/1988 | Korteweg | 128/766 |
| 4,616,642 | 10/1986 | Martin et al. | 604/356 |
| 4,700,714 | 10/1987 | Fuisz | 604/322 |
| 4,725,270 | 2/1988 | Schuldt et al. | 128/849 |
| 4,798,599 | 1/1989 | Thomas . | |
| 4,966,168 | 10/1990 | Glassman | 128/849 |

FOREIGN PATENT DOCUMENTS 421334  2/1911  France ................................ 604/49

Primary Examiner—David Isabella
Assistant Examiner—K. Reiche
Attorney, Agent, or Firm—King & Schickli

[57] ABSTRACT

An irrigation solution collection device is provided including an outer sheath formed of substantially water impervious material and an inner collecting and draining section formed of capillary matting material. The device includes proximal and distal ends with the collecting and draining section of capillary matting material being exposed at the proximal end for collecting irrigation solution from a selected site. This irrigation solution is then drawn through the sheath to the distal end for delivery to a collection receptacle. Preferably, the proximal end of the device is substantially U-shaped so as to surround the site from which irrigation solution is to be collected. Additionally, the flow rate of the capillary matting material through the sheath is increased by forming the collecting and draining section from a plurality of strips of capillary matting material that flare outwardly from substantially adjacent the proximal end to the distal end. In accordance with an additional aspect of the present invention, an irrigation system is provided. The system includes a mechanism for irrigating a selected site with an irrigation solution in conjunction with a collection device.

11 Claims, 2 Drawing Sheets

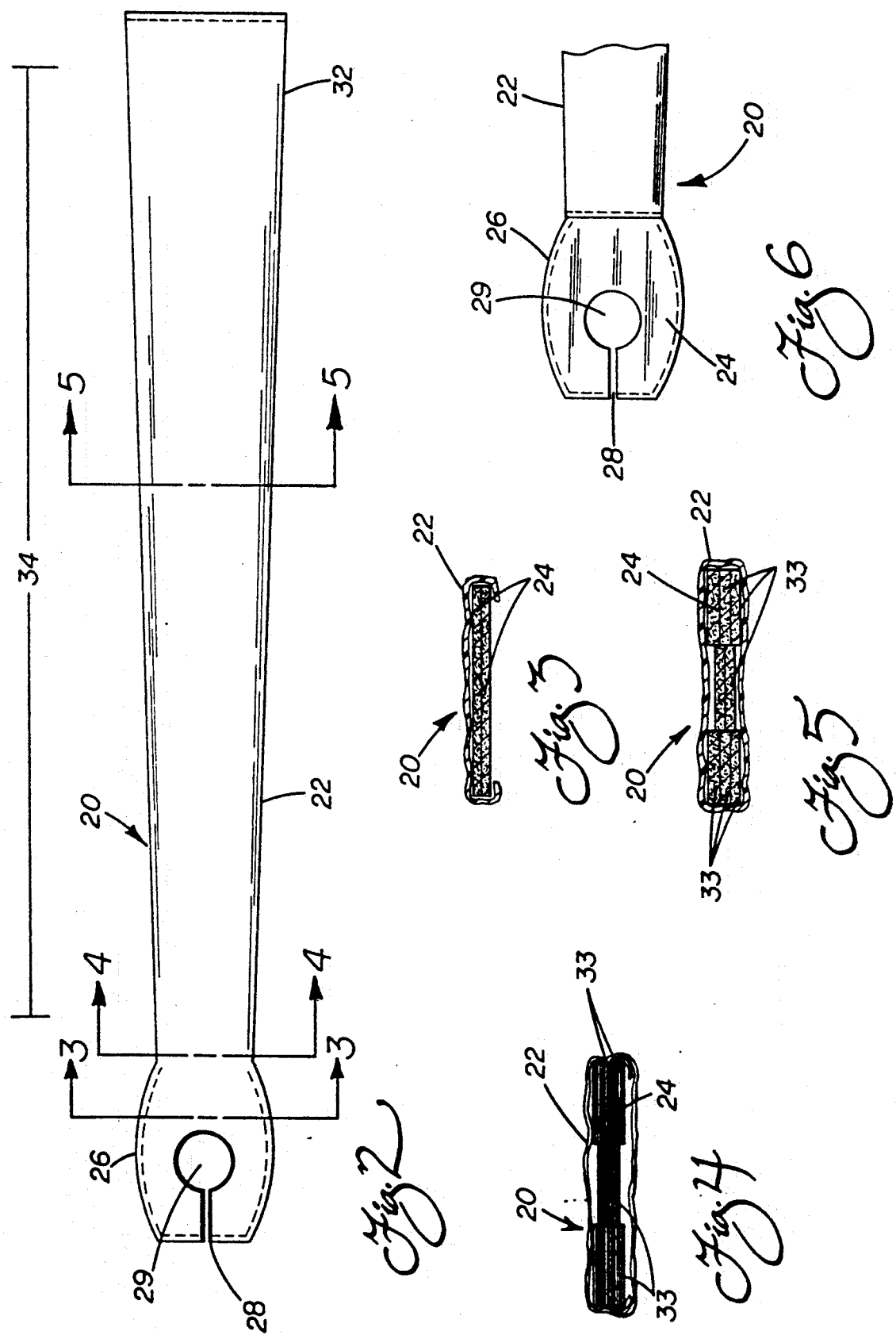

IRRIGATION SOLUTION COLLECTION DEVICE

TECHNICAL FIELD

The present invention relates generally to irrigation devices and, more particularly, to an irrigation solution collection device including such a device specifically adapted for treating the eye of a patient.

BACKGROUND OF THE INVENTION

The accidental introduction of foreign material into an eye may often lead to temporary or even permanent sight impairment and possibly total loss of sight. Troublesome eye infections are also quite painful and may, if left untreated, lead to permanent damage to the sight. The irrigation of an injured or infected eye with an appropriate solution such as lactated Ringers IV solution, is known to be effective in initiating treatment and relieving pain.

More specifically, U.S. Pat. No. 3,664,340 to Morgan discloses an eye irrigation system wherein irrigation solution is fed from a container through a tube to a sclera lens that is positioned over the cornea of an injured eye. The solution serves to provide a continuous lavage over the surface of the eyeball which relieves pain and washes foreign material from the eye.

While this device has been particularly effective in treating eye injuries and eye infections, it does suffer a number of drawbacks. More particularly, the outflow of solution from the eye must be absorbed with toweling. Unfortunately, any movement of the toweling in an area of an injured eye may result in the inadvertent subjecting of a patient to undesired trauma. Additionally, it should be appreciated that the irrigation process may be a lengthy one lasting 24 hours or more. Accordingly, an attendant must be available to check the toweling and be sure that the irrigation solution is being absorbed throughout this period. This, of course, is a time consuming, labor intensive job that adds significant expense to the treatment procedure.

Recognizing these difficulties, research efforts have culminated in the development of an eye irrigating-/washing apparatus in the form of a goggle as disclosed in U.S. Pat. No. 4,798,599 to Thomas. The apparatus disclosed in Thomas includes an eye cup that is positioned over the eye so as to form a liquid confining chamber adjacent the eye. More particularly, skin above and below the eye is drawn away from the eye with the eye cup being pushed against the skin so that the rim of the cup applies sufficient pressure to hold the eye open. Eye wash is delivered to the chamber by inlets and an appropriate outlet is provided that connects to a conduit that drains the wash from the eye to a receiving receptacle.

While this device provides effective eye irrigation, it also is not without its drawbacks. More particularly, the device is difficult to properly position for effective operation. It should be appreciated that time lost in the positioning of the device may be critical in preventing permanent injury to the sight of the patient. It should also be appreciated that movement of the head of the patient or any inadvertent bumping of the device is prone to cause the cup to become unseated, resulting in solution flowing out from around the rim of the cup over the face of the patient. Further, even when seated properly, some solution is prone to flow through the border between the rim and the face of the patient particularly near the outer edge of the eye. Accordingly, a need is identified for an improved irrigation system and, more particularly, an irrigation solution collection device. Preferably, the collection device should also have sufficient versatility to be useful for other medical and dental applications.

SUMMARY OF THE INVENTION

Accordingly, it is a primary object of the present invention to provide an irrigation solution collection device and an irrigation system for treating a patient overcoming the above-described limitations and disadvantages of the prior art.

Another object of the present invention is to provide an economical and efficient irrigation solution collection device that substantially reduces treatment costs. The device also is convenient to utilize and is versatile so as to be adaptable for use in a number of different medical and dental procedures.

An additional object of the present invention is to provide an irrigation solution collection device and irrigation system for treating the eye of a patient that substantially avoids the unnecessary application of trauma to the area surrounding the eye. Accordingly, the irrigation system of the present invention serves to relieve the patient with a soothing flow of irrigation solution which is then absorbed from the area of the eye and drawn away from the face of the patient through a unique collection device.

Yet another object of the invention is to provide an irrigation solution collection device and irrigation system that effectively collects irrigation solution from the eye and eliminates the need to handle non-sterile and possibly contaminated fluid thereby preventing that fluid from coming into contact with medical personnel and other parts of the body of the patient.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved irrigation solution collection device is provided. The collection device includes an outer sheath formed of substantially water impervious material such as nylon or polyethylene sheet. The device also includes an inner collecting and draining section that is preferably formed of capillary matting material such as has long been utilized in the gardening industry to draw water from a source to a series of pots containing seeds or plants.

More particularly, the collection device has a proximal end and a distal end. The collecting and draining section is exposed at the proximal end for collecting irrigation solution from a selected site such as the eye of a patient. This solution collected in the exposed capillary matting material is then drawn along the matting material through the sheath to the distal end of the device for delivery to a receiving receptacle.

Preferably, the proximal end of the device is substantially U-shaped so as to surround the site from which irrigation solution is to be collected. Further, the flow rate of the collecting and draining section of the device is increased by forming the median portion and distal end from a plurality of strips of capillary matting material. This advantageously serves to increase the area of material directly exposed to the irrigation solution. Additionally, the capillary matting material is flared from substantially adjacent the proximal end all the way to the distal end so as to increase the solution drawing action of the collecting and draining section. In this way, the collection and flow rate of the device are increased so as to allow irrigation of a trauma site such as the eyes with a faster flushing stream of irrigating solution that may be completely managed and collected by the irrigation collection device.

In accordance with yet another aspect of the present invention, an irrigation system is provided for treating the eye of a patient. The irrigation system includes a source of irrigation solution such as an IV bottle or bag of lactated Ringers solution. A scleral lens is also provided. As is known in the art, the scleral lens is positioned under the eyelids over the cornea of the eye of the patient receiving treatment. The system also includes means for feeding irrigation solution from the source to the scleral lens. More particularly, the feeding means includes tubing and a solution metering device. An example of such a commercially available device is the Morgan Lens Delivery Set. Finally, the irrigation system includes an irrigation solution collection device of the type described above.

In accordance with yet another aspect of the present invention, an irrigation system for medical and dental applications is also provided. This irrigation system includes means for irrigating a selected site with irrigation solution as well as means for collecting the solution from the irrigation site. The collecting means includes a collecting and draining section formed from capillary matting material at least partially received within an outer sheath of water impervious material as described above in greater detail.

Still other objects of the present invention will become readily apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated in and forming a part of the specification, illustrates several aspects of the present invention and together with the description serves to explain the principles of the invention. In the drawing:

FIG. 2 is a top plan view of the irrigation solution device of the present invention;

FIG. 3 is a cross section of the irrigation solution collection device shown through line 3—3 in FIG. 2;

FIG. 4 is a cross section of the irrigation solution collection device shown through line 4—4 in FIG. 2;

FIG. 5 is an additional cross section of the irrigation solution collection device shown in FIG. 3 through line 5—5 of FIG. 2, and FIG. 6 is a fragmentary bottom plan view of the collection device shown in FIG. 2.

Figure 1:
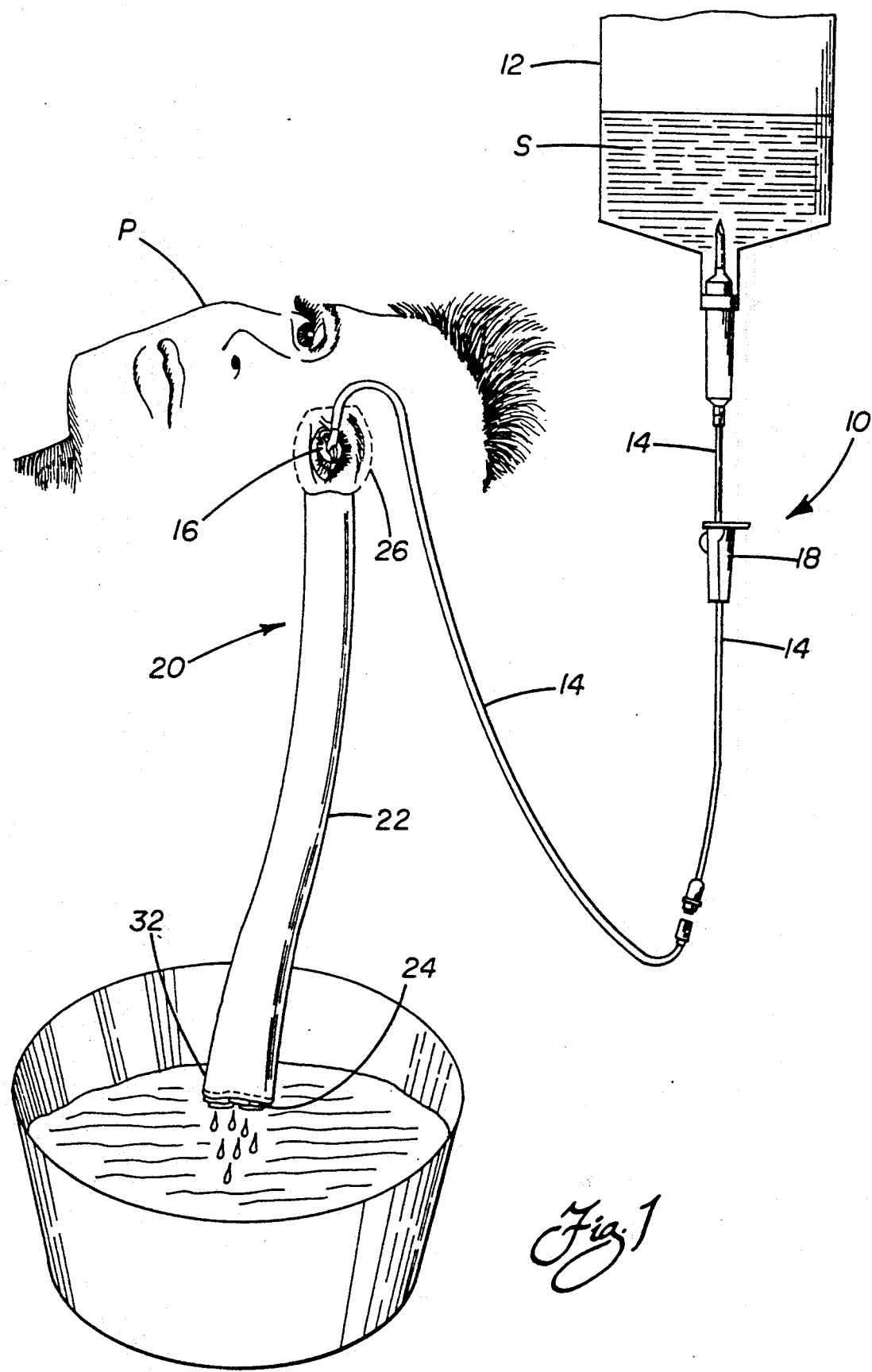
FIG. 1 is a perspective view of the irrigation system of the present invention for treating the eye of a patient.

Reference will now be made in detail to the present preferred embodiment of the invention, an example of which is illustrated in the accompanying drawing.

DETAILED DESCRIPTION OF THE INVENTION

Reference is now made to FIG. 1 showing the irrigation system 10 of the present invention for treating the eye of a patient P. As shown, the irrigation system 10 includes a source 12 of irrigation solution S such as the IV bag. As is known in the art, the irrigation solution may be lactated Ringers solution, a lactated Ringers solution with suitable antibiotic and steroid, a solution of preferred ocular antiseptic or any other solution for flushing and treating an ocular injury due to, for example, acid burns, solvents, gasolines, detergents, alkaline burns, non-imbedded foreign bodies and infections. The irrigation solution may also be utilized as a routine pre-operative and/or post-operative treatment.

The solution S is fed through tubing 14 to a scleral lens 16. As is known in the art, the scleral lens 16 is positioned under the upper and lower eye lids so as to rest over the cornea of the patient P. As is further known in the art, the irrigation solution is metered through the tubing 14 with the rate of flow being controlled by means of the infinitely adjustable clamp 18.

As the irrigation solution S flows through the tubing 14 to the scleral lens 16, it is directed over the cornea of the eye undergoing treatment. This solution S serves to flush the cornea, conjunctiva and conjunctival folds of the inner eyelid thereby removing any foreign body or contaminant. Of course, medicine may also be provided to the ocular tissues through the irrigation solution to aid in the treatment of infection or to otherwise treat eye trauma.

As the solution S flows from the eye with any entrapped foreign bodies, it is drawn into the irrigation solution collection device 20. The irrigation solution collection device 20 of the present invention includes an outer sheath 22 formed of a substantially water impervious material. Preferably, the sheath is seamless and constructed of nylon. Other materials may, however, be utilized such as polyethylene.

As best shown in FIGS. 3-6, the sheath 22 surrounds and may be sewn to an inner collecting and draining section 24 formed of capillary matting material. Preferably, the capillary matting material is formed from non-woven, man-made fabric. The fibers of the fabric are non-absorbent and run in irregular patterns. These create thousands of small spaces which hold solution and through which solution may move by capillary action. Preferably, the capillary matting material provides a flow rate of up to 500 ml per hour or more. This type of capillary matting material is commercially available under the HUMEX MATTING trademark.

As best appreciated from viewing FIGS. 2-6, the proximal end 26 of the collection device 20 is substantially U-shaped. The opening 28 at the one end is adapted to allow the passage of the tubing 14 so that the proximal end 26 may be positioned so as to surround the site, in this case the eye, from which irrigation solution is to be collected. Once positioned over the eye, the collection device 20 may be taped to the face of the patient P in the same manner as the tubing so as to prevent inadvertent displacement of the device from its proper operative position. The opening 30 in the central portion of the proximal end 26 advantageously allows visual observation of the treatment site when desired (see also FIG. 1).

As should be appreciated from viewing FIGS. 3-6, the bottom of the proximal end 26 includes an exposed section of capillary matting material 24. The exposed section of capillary matting material is positioned face down around the irrigation site so that irrigation solution S flowing from the eye is drawn directly into the capillary matting material.

As best shown in FIGS. 2 and 3-5, the collection device 20, including the sheath 22 and capillary matting material 24, flares outwardly from the proximal end 26 to the distal end 32. Additionally, throughout the median portion 34 and at the distal end 32, the capillary matting material 24 is in the form of multiple strips 33 so as to increase the area of material directly exposed to the irrigation solution. Advantageously, the strips 33 and the flaring serve to increase the drawing force of the capillary matting material 24 and hence the flow rate. Accordingly, irrigation solution is rapidly drawn from the exposed proximal end of the capillary matting material 24 downwardly through the median portion 34 to the distal end 32 of the collection device 20. Further, it should be appreciated that the face of the patient is protected from contact with the irrigation solution S including any contaminants contained therein by the presence of the water impervious sheath 22 that completely surrounds the median portion 34 and distal end 32 of the collection device 20 (note FIGS. 2, 4 and 5).

The distal end 32 of the collection device 20 may be extended into a receptacle such as a beaker or bucket 36 which is adapted to receive and retain the irrigation solution drawn off by the collection device from the eye of the patient. Accordingly, it is unnecessary for medical personnel to come into intimate contact with the irrigation solution and any contaminants contained therein including any infectious components of that solution.

Where desired, the receptacle 36 may further be connected to a suction device (not shown) to further increase the solution drawing capacity/flow rate of the collection device 20.

In summary, numerous benefits result from employing the concepts of the present invention. By utilizing the irrigation system including the collection device of the present invention, irrigation solution is collected as it flows out from the treatment site without requiring the attention of a nurse or technician. Further, by eliminating the need to have a nurse or technician absorb the outflow of irrigation solution with towels, inadvertent and unnecessary trauma to the treatment site from blotting and manipulation of the towels is avoided. Accordingly, patient comfort is maximized and valuable staff time is saved. Additionally, it should be appreciated that the device of the present invention eliminates the need to handle sterile and possibly contaminated fluid. Further, the water impervious sleeve of the collection device serves to prevent the fluid from contacting other parts of the patient's body so as to maintain patient comfort and prevent the possible spread of infection.

The foregoing description of a preferred embodiment of the invention has been presented for purposes of illustration or description. It is not intended to be exhaustive or to limit the invention to the precise form disclosed. Obvious modifications or variations are possible in light of the above teachings. For example, removal of unwanted fluids from an area during surgery or treatment without the need for suction or the repeated utilization of sponging is possible utilizing the collection device of the present invention. Additionally, the collection device could be utilized to manage fluids during dental work. More specifically, an exposed section of capillary matting material could be utilized to draw the unwanted fluid from the site during routine and/or specialized procedures without the trauma and inconsistency of a suction device. Accordingly, patient comfort would be enhanced and staff time would be saved.

The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally and equitably entitled.

I claim:

1. An irrigation solution collection device, comprising:
    an outer sheath formed of substantially water impervious material; and
    an inner means for collecting and draining irrigation solution formed of capillary matting material received within said outer sheath;
    said device having a proximal end and a distal end with said means for collecting and draining including a surface exposed by said outer sheath at said proximal end for collecting irrigation solution from a selected site, said means for collecting and draining being flared from substantially adjacent said proximal end to said distal end so as to increase the solution draining action, said solution being drawn through said means for collecting and draining received in said outer sheath to said distal end.

2. The collection device set forth in claim 1 wherein said outer sheath is constructed from plastic.

3. The collection device set forth in claim 1, wherein said outer sheath is constructed from nylon.

4. The collection device set forth in claim 1, wherein said outer sheath is seamless.

5. The collection device set forth in claim 1, wherein said inner means for collecting and draining provides a flow rate of at least 500 ml per hour.

6. The collection device set forth in claim 1, wherein said capillary matting material is formed from nonwoven, man-made fabric.

7. The collection device set forth in claim 1, wherein said proximal end of said device is substantially U-shaped.

8. The collection device set forth in claim 1, wherein said device includes a median portion between said proximal and distal ends, said median portion and said distal end of said means for collecting and draining irrigation solution are formed from a plurality of strips of capillary matting material to increase the area of material directly exposed to irrigation solution.

9. An irrigation system for treating the eye of a patient comprising:
    a source of irrigation solution;
    a scleral lens including means for positioning said scleral lens over the cornea of the eye of the patient;

means for feeding irrigation solution from said source to said scleral lens;

means for collecting said irrigation solution from said eye including a collecting and draining section having a proximal end, a median portion and a distal end formed of capillary matting material, said capillary matting material being flared from said proximal end toward said distal end so as to increase the solution draining action of said material; said collecting and draining section further including an outer sheath formed of substantially water impervious material and said proximal end including means for attaching said collecting means about said eye.

10. The irrigation system of claim 9, wherein said capillary matting material is exposed at said proximal end and said attaching means is substantially U-shaped.

11. The irrigation system of claim 10, wherein said capillary matting material in said median portion and distal end of said collecting means is formed in strips connected together at said proximal end.

* * * * *